United States Patent [19]

Bundgaard et al.

[11] Patent Number: 5,405,834
[45] Date of Patent: Apr. 11, 1995

[54] PRODRUG DERIVATIVES OF THYROTROPIN-RELEASING HORMONE (TRH)

[76] Inventors: Hans Bundgaard Tjønevej 36, Hørsholm, Denmark, 2970; Judi Møss, Helsingborggade 9, Copenhagen ∅, Denmark, 2100

[21] Appl. No.: 842,181
[22] PCT Filed: Sep. 3, 1990
[86] PCT No.: PCT/DK90/00228
§ 371 Date: Mar. 20, 1992
§ 102(e) Date: Mar. 20, 1992
[87] PCT Pub. No.: WO91/03487
PCT Pub. Date: Mar. 21, 1991

[30] Foreign Application Priority Data

Sep. 4, 1989 [DK] Denmark ............... 4372/89

[51] Int. Cl.$^6$ .............. C07K 7/04; A61K 37/24; A61K 37/43
[52] U.S. Cl. .......................... 514/18; 530/331
[58] Field of Search ............ 530/331; 514/18, 19

[56] References Cited

U.S. PATENT DOCUMENTS 4,060,603 11/1977 Morgan et al. ............... 424/177
4,564,609 1/1986 Tamura et al. ............... 514/18

FOREIGN PATENT DOCUMENTS 617667 6/1980 Switzerland.

OTHER PUBLICATIONS

Banks, W. A. & Kastin A. J.: *Brain Res. Bull.* 15, 1985, 287–292.
Bassiri, R. M. & Utiger, R. D.; *J. Clin. Invest.* 52, 1973, 1616–1619.
Bauer, K.: *Biochimie* 70, 1988, 69–74.
Bauer, K., Nowak, P. & Kleinhauf, H.: *Eur. J. Biochem.* 118, 1981, 173–176.
Bundgaard, H. & Moss J.: *J. Pharm. Sci.* 78, 1989, 122–126.
Duntas, L., Keck., F. S. & Pfeiffer, E. F.: *Dtsch. med. Wschr.* 113, 1988, 1354–1357.
Giralt, E., Ludevid, M. D. & Pedroso, E.: *Bioorg. Chem.* 14, 1986, 405–416.
Griffiths, E. C.: *Nature* 322, 1986, 212–213.
Griffiths, E. C.: *Clin. Sci.* 73, 1987, 449–457.
Gronvald, F. C., et al.: In "Peptides, Structure and Biological Function. Proceed. Amer. Pept. Symp. 7th" (Eds.: Gross, E. & Meinhofer, F.), 1979, 309–312.
Gronvald, F. C., et al.: In "Peptides, Proceed. Dur. Pept. Symp. 16th 1980" (Ed.: Brunfeldt, K.) Scriptor, Copenhagen, 1981, 706–710.
Hichens, M.: *Drug Metab. Rev.* 14, 1983, 77–98.
Iversen, E.: *J. Endocrin*, 118, 1988, 511–516.
Jackson, I. M. D.: *N. Engl. J. Med.* 306, 1982, 145–155.
Loosen, P. T.: *Prog. Neuro-Psychopharmacol. & Biol. Psychiat.*, 12, 1988, S87–S117.
Matzner, M., Kurkjy, R. P. & Cotter, R. J.: *Chem. Rev.* 64, 1964, 645–687.
Metcalf, G.: *Brain Res. Rev.* 4, 1982, 389–408.
Morley, J. E., et al.: *J. Clin. Endocrin. Metab.* 48, 1979, 377–380.
Wilk, S., Suen, C. F. & Wilk, E. K.: *Neuropeptides* 12, 1988, 43–47.

Primary Examiner—Robert J. Hill, Jr.
Assistant Examiner—Carol A. Salata
Attorney, Agent, or Firm—Jacobson, Price, Holman & Stern

[57] ABSTRACT

Compounds of formula (I), wherein $R_1$ is selected from the group consisting of an alkyl group, an aralkyl group, an alkenyl group, a cycloalkyl group, in which the alkyl, aralkyl, alkenyl or cycloalkyl group is unsubstituted or substituted with one or more substituents selected from the group consisting of a halogen atom, e.g. Cl or Br, a hydroxyl group or a straight or branched-chain alkoxy group containing from 1 to 6 carbon atoms; and the pharmaceutically acceptable acid addition salts thereof. Such compounds are prodrugs of TRH and are characterized by having a higher lipophilicity than TRH and possessing a high resistance toward degradation by TRH-inactivating enzymes. Such compounds will after administration be converted into TRH.

7 Claims, 4 Drawing Sheets

PRODRUG DERIVATIVES OF THYROTROPIN-RELEASING HORMONE (TRH)

BACKGROUND OF THE INVENTION

1. Field of the Invention

The present invention relates to novel transient prodrug forms of thyrotropin-releasing hormone (TRH; thyroliberin)(pGlu-L-His-L-ProNH$_2$), to methods for preparing the prodrug forms, to pharmaceutical compositions containing such prodrug forms, and to methods for using the prodrug forms.

For purposes of this specification, the term "prodrug" denotes a derivative of TRH which, when administered to warm-blooded animals, e.g. humans, is converted into the proven drug, i.e. TRH.

The term "transient" indicates that the conversion of the prodrug forms proceeds in such a manner that the proven drug form (parent TRH) is released, and the remaining moieties splitt off remain nontoxic or are metabolized so that nontoxic metabolic products are produced.

These novel prodrugs forms of TRH are certain N-alkoxycarbonyl derivatives of TRH which possess a desirable high lipophilicity in comparison to the parent compound, TRH, and which are capable of protecting the parent compound, TRH, against enzymatic degradation or inactivation in vivo, e.g. in the blood.

2. Description of the Prior Art

TRH is the hypothalamic peptide that regulates the synthesis and secretion of thyrotropin from the anterior pituitary gland. Since the discovery of TRH in 1969, the peptide has been shown to have not only a variety of endocrine and central nervous system-related biological activity, but also potential as a drug in the management of various neurologic and neuropsychiatric disorders including depression and schizophrenia (see e.g. Metcalf, 1982; Jackson, 1982; Griffiths, 1986, 1987; Loosen, 1988). However, the clinical utility of TRH has been hampered by its rapid metabolism and clearance and its poor access to the brain (cf. e.g., Metcalf, 1982; Hichens, 1983; Griffiths, 1987). The poor penetration of TRH of the bloodbrain barrier is largely due to its very low lipophilicity (Banks & Kastin, 1985). Intravenous studies in rats and humans have shown that TRH has a plasma half-life of only 4–6 min (Bassin & Utiger, 1973; Morley et al., 1979; Duntas et al., 1988; Iversen, 1988). This short biological half-life is mainly due to rapid degradation of the tripeptide by enzymes endogenous to all body fluids and tissues, in particular by pyroglutamyl aminopeptidases including the so-called TRH-specific pyroglutamyl aminopeptidase serum enzyme (Bauer et al., 1981; Bauer, 1988; Wilk et al., 1988). The latter enzyme plays a major role in the rapid metabolism of TRH in human plasma (Bauer, 1988).

Accordingly, there is a need in the art to circumvent these problems of rapid enzymatic inactivation and poor lipophilicity of TRH.

It has now been found that it is possible to protect TRH against enzymatic inactivation and improve the lipophilicity by the prodrug approach according to the present invention.

SUMMARY OF THE INVENTION

The compounds of the present invention are N-alkoxycarbonyl derivatives of TRH which are more lipophilic than the active parent drug and hence better able to penetrate the blood-brain barrier than TRH, which afford protection of TRH against enzymatic inactivation in vivo and which, upon administration to warm-blooded animals, e.g. humans, are slowly converted into the active parent TRH resulting in enhanced duration of action. These characteristics make the compounds useful as therapeutic agents.

The compounds of the present invention are represented by the following general formula I and wherein R$_1$ is selected from the group consisting of an alkyl group, an aralkyl group, an alkenyl group, a cycloalkyl group, in which the alkyl, aralkyl, alkenyl or cycloalkyl group is unsubstituted or substituted with one or more substituents selected from the group consisting of a halogen atom, e.g. Cl or Br, a hydroxyl group or a straight or branched-chain alkoxy group containing from 1 to 6 carbon atoms; and the pharmaceutically acceptable acid addition salts thereof.

In the present context, the term "alkyl" designates C$_{1-15}$ alkyl which may be straight or branched, such as methyl, isopropyl, octyl, or decyl. The term "alkenyl" designates a C$_{2-15}$-monounsaturated aliphatic hydrocarbon group which may be straight or branched, such as propenyl or pentenyl. The term "cycloalkyl" designates a radical containing 4 to 7 carbon atoms, e.g. cyclohexyl. The term "aralkyl" designates a radical of the type -alkylene-aryl, wherein aryl encompasses radicals such as phenyl and naphthyl and the alkylene moiety contains 1 to 6 carbon atoms and can be straight or branched-chain, e.g. methylene, and the like.

TRH exists in two tautomeric forms, the N(1)-H-tautomer (a) and the N(3)-H-tautomer (b):

(a) ⟷ (b)

In neutral aqueous solution the tautomeric equilibrium of TRH is shifted toward the N(3)-H form (Giralt et al., 1986). It is known that acylation of the imidazole group in various histidine derivatives by reaction with chloroformates can occur both at N(1) and N(3). Thus, whereas acylation of α-amino protected histidine derivatives with isobutyl chloroformate has been shown to result in the exclusive formation of N(3)-substituted isobutyloxycarbonyl derivatives, reaction of the same derivatives with adamantyloxycarbonyl fluoride results in an isomeric mixture consisting of N(1)- and N(3)-substituted derivatives in the ratio 1:2 (Gronvald et al., 1979, 1981).

In the present invention, the term "N-alkoxycarbonyl derivatives of TRH" encompasses both N(1)- and N(3)-substituted derivatives, or a mixture thereof, as shown in formula I, the substitution being at one of the nitrogen atoms of the imidazole moiety of TRH.

The term "non-toxic pharmaceutically acceptable acid addition salts" as used herein generally includes the non-toxic acid addition salts of compounds of formula I, formed with non-toxic inorganic or organic acids. For example, the salts include those derived from inorganic acids such as hydrochloric, hydrobromic, sulphuric, sulphamic, nitric, phosphoric and the like; and the salts with organic acids such as acetic, propionic, succinic, fumaric, maleic, tartaric, citric, glycolic, lactic, stearic, malic, pamoic, ascorbic, phenylacetic, benzoic, glutamic, salicylic, sulphanilic, methansulphonic, and the like.

In another aspect the invention relates to pharmaceutical compositions comprising a pharmaceutically acceptable carrier or excipient and a compound of the formula I, and the therapeutic use of such compositions.

In a further aspect the invention also concerns a method for preparing compounds of the formula I.

In recent years, several analogs of TRH have been prepared in order to circumvent the problem of the rapid metabolism of TRH by endogenous enzymes. A great number of these analogs are, like TRH, tripeptides containing a L-histidyl residue with an unsubstituted imidazole group, for example the compounds CG 3509, CG 3703, RX 77368, DN 1417, MK-771, YM-14673 and pGlu-His-(3,3'-dimethyl)ProNH$_2$ but these compounds also suffer from metabolic instability in varying degree and from limited lipophilicity and hence poor access to the brain (Metcalf, 1982; Hichens, 1983).

TM 14673

The prodrug principle described herein is also applicable to such TRH analogs (i.e.. tripeptides containing a histidine residue with a free imidazole group) and accordingly. N-alkoxycarbonyl derivatives formed at the imidazole group of such TRH analogs are also considered as part of the present invention.

DETAILED DESCRIPTION OF THE INVENTION

As examples of the compounds of formula I may be mentioned compounds in which $R_1$ is one of the following groups: methyl, ethyl, propyl, isopropyl, butyl, sec. butyl, pentyl, hexyl, heptyl, octyl, nonyl, decyl, pentadecyl, t.-butyl, allyl, 8-hydroxyoctyl, 2-chloroethyl, 8-isopropoxyoctyl, benzyl, phenethyl, 2-butenyl, cyclohexyl or cyclopentyl.

The prodrug compounds of formula I of the present invention can be used to treat any condition for which the parent TRH is useful. The compounds may be administered orally, topically, parenterally, rectally, buccally, or by inhalation spray in dosage forms or formulations containing conventional, non-toxic pharmaceutically acceptable carriers, adjuvants or vehicles. The preferred route of administration is by parenteral injection.

The compounds of the present invention may be prepared by various methods. One method comprises reacting TRH with a compound of the formula II

II wherein $R_1$ is as defined above and X is a leaving group. As examples of leaving groups X may be mentioned chlorine, bromine, iodine, fluorine, and 4-nitrophenyloxy. A preferred leaving group is chlorine. The reaction is conveniently carried out in a solvent such as dioxane, acetone, acetonitrile, N,N-dimethylformamide, tetrahydrofuran, pyridine or the like, or in water or mixtures of water-aprotic solvents, at a temperature of from −10° C. to 80° C., for from ½ to 72 h. The reaction is preferably conducted in the presence of a base such as an alkali metal carbonate or an organic base such as triethylamine or pyridine.

Several compounds of formula II in which X is chlorine and methods for preparing them are known from the literature, see e.g. Matzner et al. (1964).

Another method for preparing the compounds of the present invention comprises reacting TRH with an alkoxyformic anhydride of the formula III $(R_1OCO)_2O$     III wherein $R_1$ is as defined above. The reaction is conveniently carried out in water or mixtures of water-aprotic solvents.

To form acid addition salts of the compounds of formula I said compounds are treated with suitable pharmaceutically acceptable inorganic or organic acids by standard procedures.

The present invention is further illustrated by the following examples which, however, are not construed to be limiting. Chromatographical data of the prepared compounds are given in Table 1. As indicated above reaction of TRH with chloroformates may result in either N(1)- or N(3)-substitution at the imidazole group. However, the compounds described in the following examples consisted predominantly (>90%) or entirely of a single product as determined on basis of HPLC analysis and kinetic experiments. The products are believed to be N(3)-substituted derivatives.

EXAMPLE 1

N-Octyloxycarbonyl TRH (Formula I; $R_1$=octyloxy)

To a solution of TRH (3 mmol, 1.09 g) in 10 ml of N,N-dimethylformamide was added 3.6 mmol (0.51 ml) of triethylamine followed by 3.6 mmol (0.72 ml) of n-octyl chloroformate. The mixture was stirred at room temperature for 2.5 h, poured into 60 ml of water and then extracted with ethyl acetate (2×75 ml). The combined ethyl acetate extracts were washed with water (2×50 ml), dried over anhydrous sodium sulphate and evaporated in vacuo. The residue obtained was recrystallized from ethyl acetate-ether-petroleum ether to give the title compound in a yield of 70%. Mp. 79°-82° C.

Anal.: Calc. for $C_{25}H_{38}N_6O_6$, $1H_2O$: C, 55.96; H, 7.51; N, 15.66. Found: C, 56.07; H, 7.69; N, 15.44.

EXAMPLE 2

N-Octyloxycarbonyl TRH, hydrochloride salt (Formula I; $R_1$=octyl)

The compound obtained as described in Example 1 was dissolved in ethyl acetate (2 ml) and 0.25 ml of a 2.5M methanolic HCl solution was added. By subsequent addition of ether and petroleum ether the title compound precipitated. After standing at −20° C. for 4 h the precipitate was filtered off, washed with ether and dried in vacuo over phosphorous pentoxide. Yield: 85%.

EXAMPLE 3

N-Hexyloxycarbonyl TRH (Formula I; $R_1$=hexyl)

To a mixture of TRH (1 mmol, 362 mg) in 20 ml of acetonitrile was added 1.2 mmol of triethylamine followed by 1.2 mmol of n-hexyl chloroformate. The mixture was stirred at room temperature for 5 h and evaporated under reduced pressure. The residue obtained was taken up in water (10 ml) and ethyl acetate (20 ml). The organic phase was separated and the aqueous phase reextracted with 20 ml of ethyl acetate. The combined extracts were washed with a 2% sodium bicarbonate solution followed by water, dried over anhydrous sodium sulphate and evaporated under reduced pressure. The residue obtained was recrystallized from ethanol-ether-petroleum ether and finally dried in vacuo over phosphorous pentoxide to give the title compound in a yield of 67%. Mp. 71°–73° C.

Anal.: Calc. for $C_{23}H_{34}N_6O_6$, $1H_2O$: C, 54.32; H, 7.14; N, 16.52. Found: C, 54.20; H, 7.25; N, 16.40.

EXAMPLE 4

By following the procedures of Example 1 and 3 and using the appropriate, chloroformate several more N-alkoxycarbonyl derivatives of TRH accodring to this invention are obtained. The structure and properties of these derivatives are shown in Table 1.

Lipophilicity of the TRH prodrugs

The lipophilicity of the derivatives of the present invention and of TRH was assessed by measuring the apparent partition coefficients (P) of the compounds between 1-octanol and 0.02M phosphate buffer of pH 7.4. The log P values obtained are shown in Table 1. The results obtained show clearly that it is readily feasible to obtain prodrug derivatives possessing a much higher lipophilicity than the parent TRH. It is also apparent that by selecting an appropriate $R_1$-substituent of the compounds of formula I it is readily possible to obtain prodrug derivatives with varying and any desirable lipophilicity.

The chromatographic capacity factor obtained by reversed-phase column chromatography is also a commonly used measure for the relative lipophilicities of various compounds. The capacity factor k′ of a solute is defined as:

$$k' = (t_r - t_0)/t_0$$

where $t_r$ is the retention time of the solute and $t_0$ is the elution time of the solvent. With a mobile phase system consisting of methanol-0.1% phosphoric acid (1:20 v/v) containing $10^{-3}$M triethylamine and using a Nova-PAK CN HP Radial Pak reversed-phase column (8×100 mm)(Waters Ass.) the various derivatives showed the k′ values given in Table 1. These data also illustrate the increased lipophilicity of the N-alkoxycarbonyl derivatives relative to the parent TRH.

Bioconversion and Stability of the Prodrugs

Reaction Conditions

Solutions of various compounds of formula I in aqueous buffer solutions or 80% human plasma solutions as well as in a buffer solution (pH 7.4) containing pyroglutamyl aminopeptidase (a calf liver preparation obtained from Boehringer, Mannheim, F.R.G.) were kept at 37° C. The initial concentration of the derivatives was in the range $10^{-5}$–$10^{-3}$M. At various times an aliquot of the solutions was withdrawn and analyzed by HPLC for remaining (intact) derivative as well as for TRH. For the plasma solutions the aliquot (250 μl) withdrawn was added to 500 μl of a 2% solution of zinc sulphate in methanol-water (1:1 v/v) in order to deproteinize the plasma. After mixing and centrifugation for 3 min at 13,000 rpm, 20 μl of the clear supernatant was analyzed by HPLC as described above. The reaction conditions used for the studies with the pyroglutamyl aminopeptidase enzyme were identical to those previously described by Bundgaard & Moss (1989).

Analytical Method

An HPLC method was used for the determination of TRH and its derivatives. In this method a reversed-phase column described above was eluted at ambient temperature with mobile phase systems consisting of 10–50% v/v acetonitrile in 0.1% phosphoric acid with triethylamine added in a concentration of $10^{-3}$M, the concentration of acetonitrile being adjusted for each compound to give an appropriate retention time (3–8 min). For the determination of TRH formed upon hydrolysis of the various derivatives a mobile phase system consisting of acetonitrile-0.1% phosphoric acid (1:20 v/v) containing 10M triethylamine was used. The flow rate was 1.5 ml min and the column effluent was monitored at 215 nm. Quantitation of the compounds was done by measuring the peak heights in relation to those of standards chromatographed under the same conditions.

The cleavage of the derivatives displayed strict first-order kinetics in all reaction solutions. Pseudo-first-order rate constants and hence the half-lives of degradation of the derivatives were calculated from the slopes of linear plots of the logarithm of remaining derivative against time.

Figure 1:
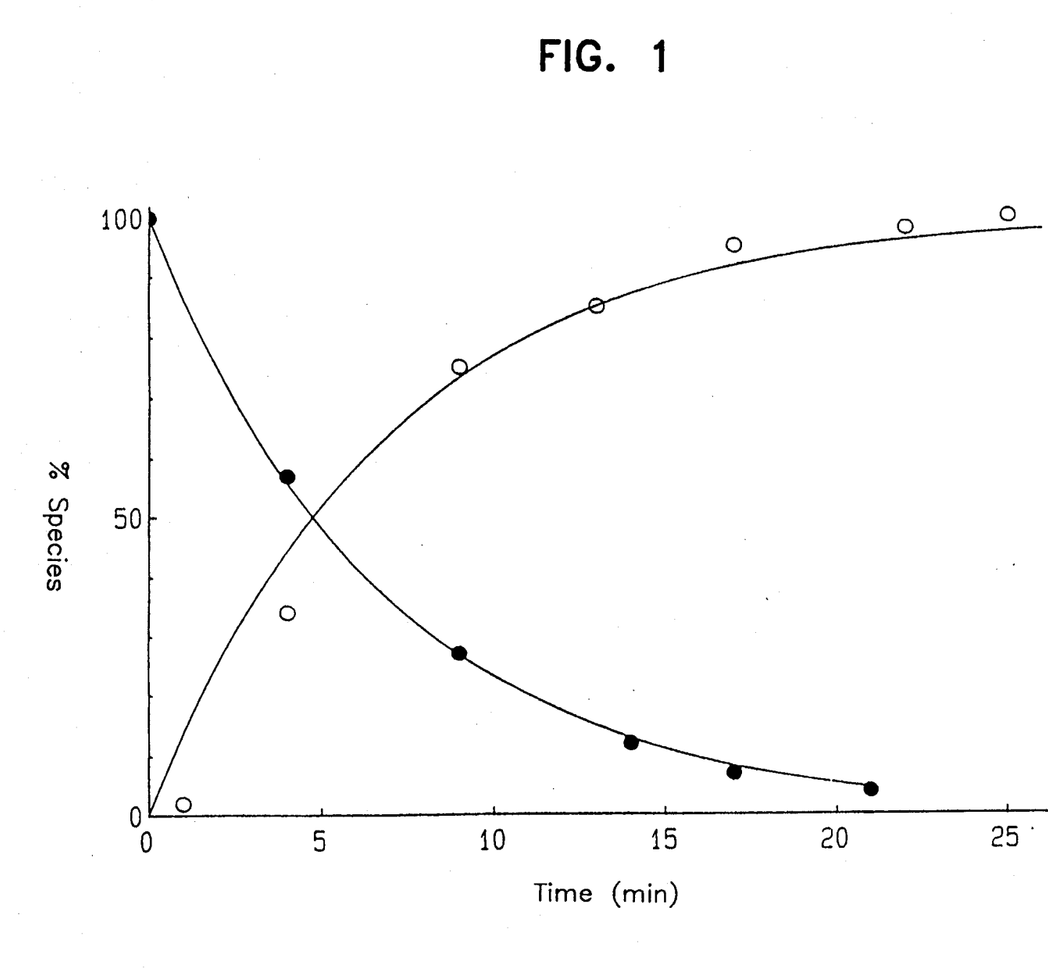
FIG. 1
Time-courses for N-octyloxycarbonyl-TRH (Formula I; $R_1$=octyl) (●) and TRH (O) during hydrolysis of the prodrug derivative in 0.02M borate buffer of pH 9.4 at 37° C.
Figure 2:
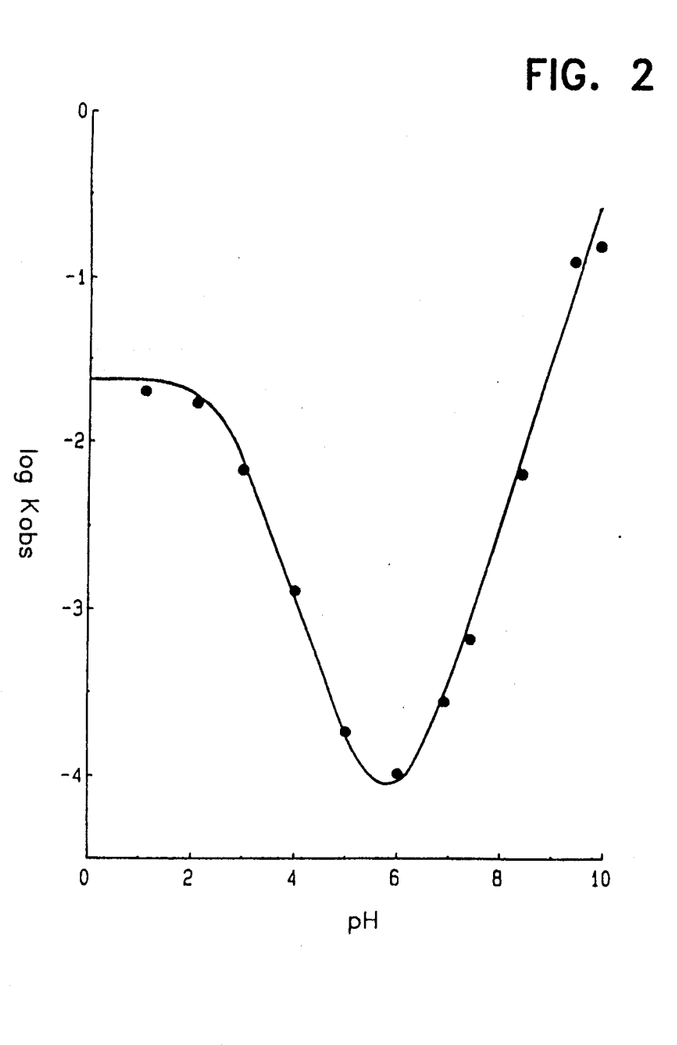
FIG. 2
The pH-rate profile for the hydrolysis of N-octyloxycarbonyl derivative of TRH (Formula I; $R_1$=octyl) in aqueous solution at 37° C.

The compounds were hydrolyzed quantitatively to TRH in aqueous solution in the pH-range 0.3–10 as shown by the example in FIG. 1. They showed maximal stability at pH 5–6, cf. FIG. 2. The time for 10% degradation of N-octyloxycarbonyl TRH in aqueous solution at pH 5.8 and 20° C. was found to be 76 h. At pH 7.4 and 37° C. the half-lives of hydrolysis ranged from 9 to 37 h (Table 2).

In the presence of pyroglutamyl aminopeptidase (PAPase I) TRH is rapidly degraded. Under conditions where TRH showed a half-life of degradation of 4 min the various N-alkoxycarbonyl derivatives proved more stable as seen from the data in Table 2.

In the presence of human plasma the N-alkoxycarbonyl derivatives showed a markedly higher stability than TRH. As seen from Table 2 the half-lives of degradation ranged from 0.5 to 6.6 h, whereas TRH degraded with a half-life of 9 min. For the consideration of the derivatives as prodrugs of TRH a crucial point is evidently their degradation pathways. Ideally, the compounds should be hydrolyzed in plasma at the imidazole-protected moiety, releasing TRH in quantitative amounts. Surprisingly, this was indeed found to be the case for the derivatives.

The reactions taking place in plasma can be illustrated as shown in Scheme 1. By virtue of spontaneous as well as plasma enzyme-catalyzed hydrolysis the N-alkoxycarbonyl derivatives are exclusively hydrolyzed at the imidazole carbamate moiety to yield TRH which subsequently degrades to yield pyroglutamic acid and L-histidyl-L-prolineamide due to the TRH-specific pyroglutamyl aminopeptidase enzyme (PAPase II) present in plasma. The latter process (i.e., degradation of TRH) showed a first-order half-life of 9 min at low TRH concentrations (less than about $2 \times 10^{-5}$M) in 80% human plasma and 37° C. whereas the degradation of TRH was found to follow zero-order kinetics at higher concentrations. In 80% human plasma and at 37° C. a zero-order rate constant of $7.2 \times 10^{-7}$M min$^{-1}$ was determined for TRH at initial concentrations of $10^{-4}$–$10^{-3}$M.

Scheme 1

The quantitative conversion of the N-alkoxycarbonyl derivatives to TRH in 80% human plasma solutions at 37° C. was demonstrated by analyzing the reaction solutions for TRH using the HPLC procedure described above.

Figure 3:
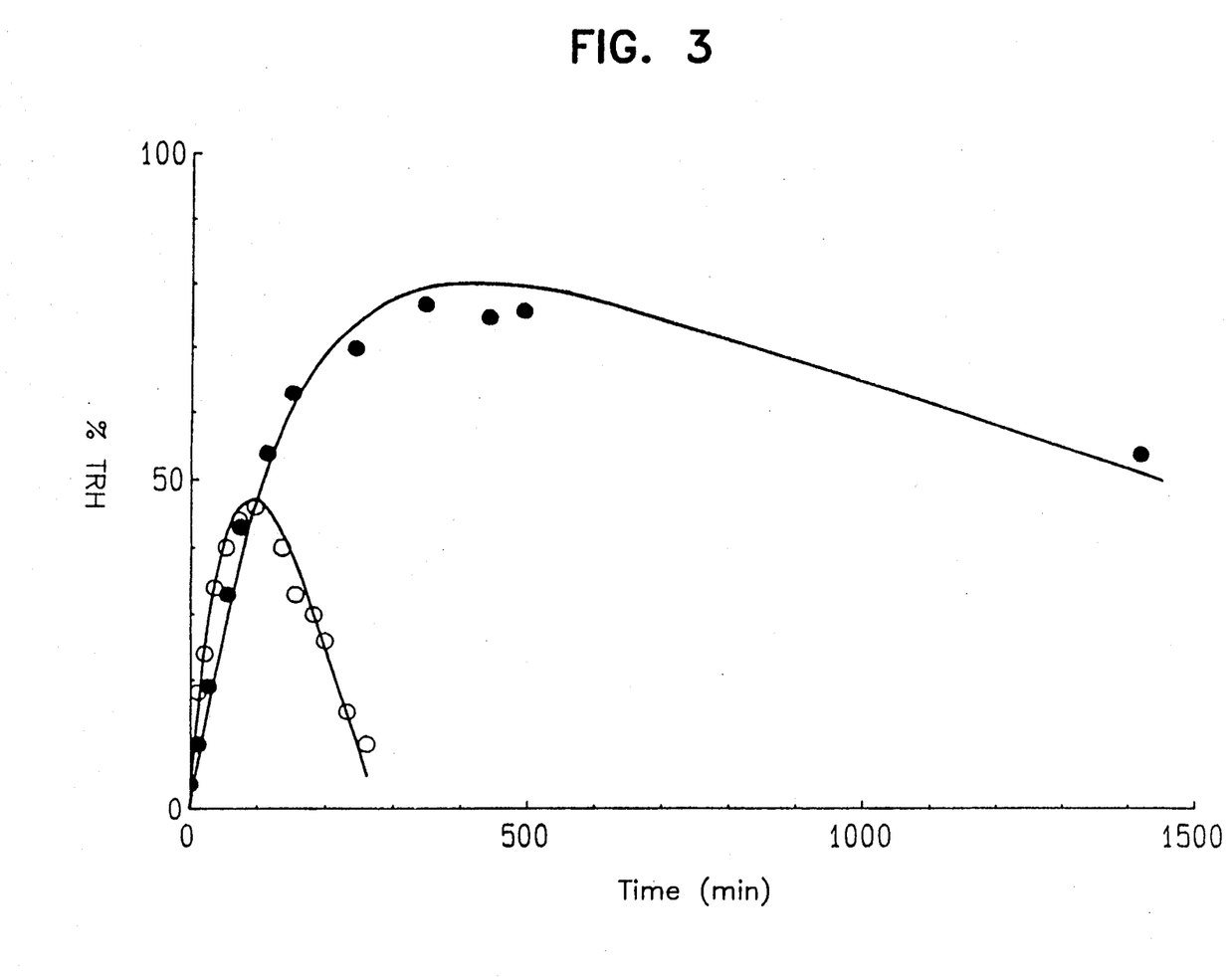
FIG. 3
Plots showing the time-course of TRH formation following incubation of N-hexyloxycarbonyl-TRH (Formula I; $R_1$=hexyl) in 80% human plasma at 37° C. at an initial concentration of the derivative of $2\times 10^{-4}$ M(●) and $10^{-3}$ M(O).
Figure 4:
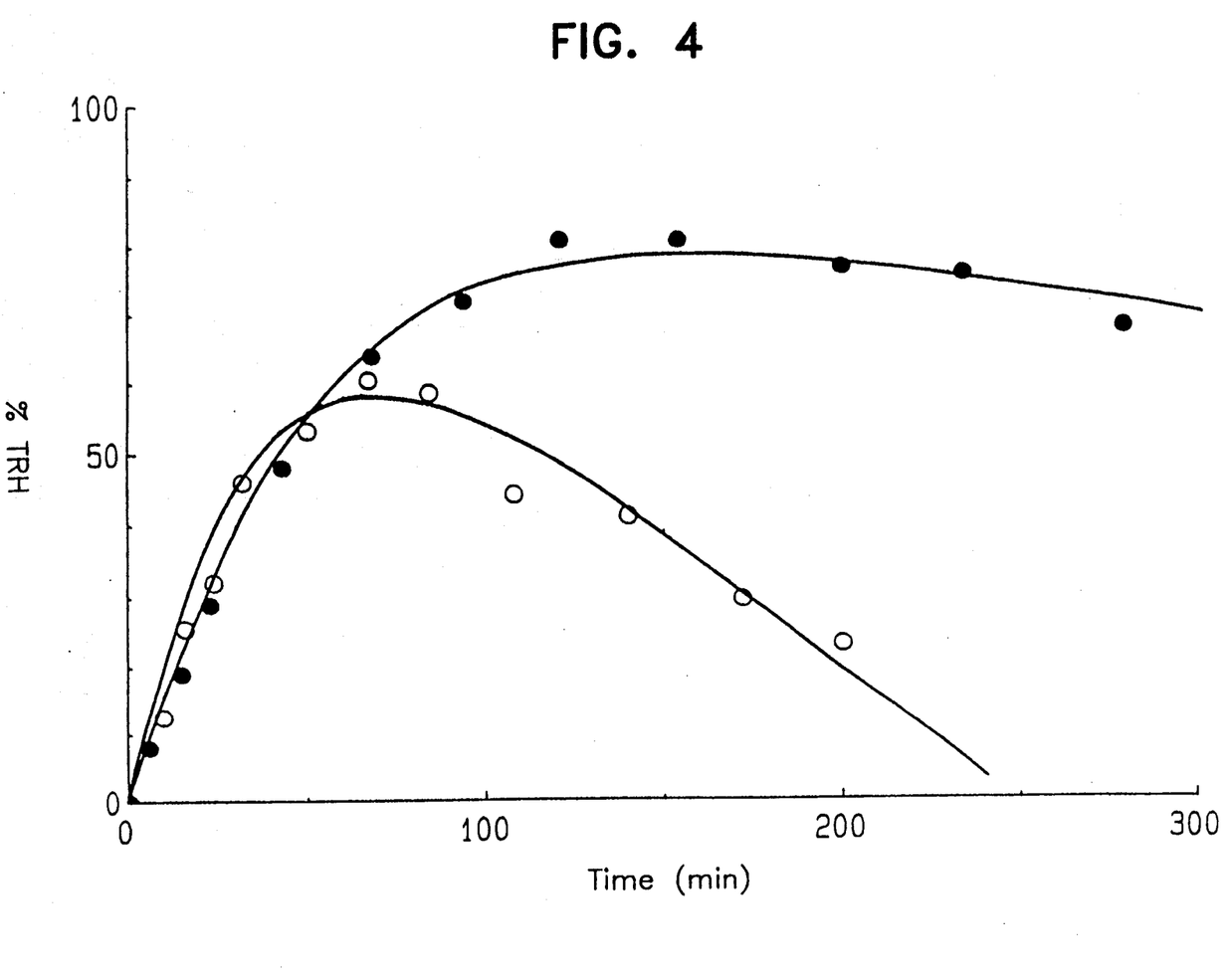
FIG. 4
Plots showing the time-course of TRH formation following incubation of N-octyloxycarbonyl-TRH (Formula I; $R_1$=octyl) in 80% human plasma at 37° C. at an initial concentration of the derivative of $2\times 10^{-4}$ M(O) and $10^{-3}$ M(●).

The data obtained for some derivatives are shown in FIGS. 3 and 4. As can be seen, TRH is formed from the derivatives in human plasma solutions. The apparent greater amounts of TRH occurring in solutions with the highest initial concentration of the derivatives is due to the fact that at the concentrations used TRH is inactivated according to zero-order kinetics, implying that the inactivation rate in terms of percentage of degradation per unit of time decreases with increasing concentration. The time-courses for TRH such as those shown in FIGS. 3 and 4 were subjected to kinetic analysis for a consecutive reaction scheme and this showed clearly that TRH is formed in stoichiometric amounts (>90%) at any varying initial derivative concentration.

These experiments demonstrate that the N-alkoxycarbonyl derivatives in fact are prodrug derivatives of TRH in that the parent active compound is released at conditions similar to those prevailing in vivo. It is also apparent that by appropriate variation of the $R_1$-substituent of the compounds of formula I it is readily possible to vary the rate of hydrolysis and hence to control and modify the rate of TRH production. Thus, more slowly hydrolyzing derivatives may function as a TRH depot, protecting the derivatized TRH against rapid enzymatic degradation in the blood.

TABLE 1

Partition coefficients (P) and chromatographic capacity factors (k') of TRH and various TRH derivatives

| Compound | log P$^a$ | log k' |
|---|---|---|
| TRH | −2.46 | <0.4 |
| $R_1$ in formula I: | | |
| CH$_3$ | 1.88 | 0.71 |
| C$_2$H$_5$ | −1.30 | 0.85 |
| CH(CH$_3$)$_2$ | −0.80 | 0.96 |
| n-C$_4$H$_9$ | −0.47 | 1.07 |
| CH$_2$CH(CH$_3$)$_2$ | −0.44 | 1.09 |
| n-C$_6$H$_{13}$ | 0.71 | 1.29 |
| n-C$_8$H$_{17}$ | 1.88 | 1.50 |
| CH$_2$C$_6$H$_5$ | −0.11 | — |
| C$_6$H$_{10}$(cyclohexyl) | 0.60 | 1.28 |
| CH$_2$CH$_2$Cl | −1.10 | — |
| CH(C$_2$H$_5$)$_2$ | 0.20 | — |
| CH(C$_3$H$_7$)$_2$ | 1.20 | — |
| CH$_2$CH(C$_2$H$_5$)C$_4$H$_9$ | 1.82 | — |

$^a$Between octanol and 0.02 M phosphate buffer pH 7.4 (21° C.).

TABLE 2

Data on the rate of hydrolysis of TRH and its various N-alkoxycarbonyl derivatives

| | Half-lives at 37° C. | | |
|---|---|---|---|
| Compound | pH 7.4 buffer | Pyroglutamyl aminopeptidase$^a$ | 80% v/v human plasma |
| TRH | — | 4 min | 9 min |
| $R_1$ in formula I: | | | |
| CH$_3$ | 9.3 h | 12 min | 2.8 h |
| C$_2$H$_5$ | 14.2 h | 23 min | 3.8 h |
| CH(CH$_3$)$_2$ | 35.8 h | 29 min | 6.6 h |
| n-C$_4$H$_9$ | 19.0 h | 11 min | 4.3 h |
| CH$_2$CH(CH$_3$)$_2$ | 19.0 h | 11 min | 4.3 h |
| n-C$_6$H$_{13}$ | 17.9 h | 8 min | 1.2 h |
| n-C$_8$H$_{17}$ | 17.5 h | 24 min | 0.5 h |
| CH$_2$C$_6$H$_5$ | 9.0 h | 7 min | −1.6h |
| C$_6$H$_{10}$ (cyclohexyl) | 36.8 h | 22 min | 6.4 h |

$^a$These data are half-lives for the degradation in buffer solution (pH 7.4) containing pyroglutamyl aminopeptidase (0.01 unit/ml).

Percutaneous Absorption of the Prodrugs

The feasibility of achieving transdermal delivery of TRH via the prodrugs of the present invention was evaluated by diffusion experiments in vitro using human skin samples.

Whole abdominal human skin obtained under autopsy was used. The skin was stored at −18° C. and was allowed to thaw gradually at room temperature before use. All subcutaneous fat was removed and the skin cut into pieces. The excised skin was mounted in open Franz diffusion cells; they had an available diffusion area of 0.70 cm$^2$. The dermal side of the skin was exposed to the receptor medium (5 ml of 0.05M isotonic phosphate buffer solution of pH 7.2) which was stirred magnetically and kept at a constant temperature of 37° C. with a circulating water bath.

The compounds were applied as 5% w/v solutions in 0.05M phosphate buffer (final pH being 6.0) or propylene glycol (100 or 200 µl). At appropriate intervals samples of 1 ml were removed from the receptor phase and replaced with fresh buffer. The samples were immediately analyzed for TRH and prodrug content by HPLC as described above. The permeation studies of each compound in each vehicle were done in triplicate.

In the case of TRH, no measurable amounts of the compound could be detected in the receptor phase during diffusion experiments lasting up to 200 h. The limit of detection of TRH was about 0.5 µg ml$^{-1}$. In contrast, the more lipophilic N-octyloxycarbonyl TRH derivative readily penetrated human skin. By applying this prodrug in an aqueous solution (pH 6.0) at a concentration of 5%, a steady-state flux of 0.044±0.006 µmol TRH/h/cm$^2$, corresponding to 16 µg TRH/h/cm$^2$, was observed. Essentially all of the prodrug applied was converted to the parent TRH during diffusion through the human skin samples. Using propylene glycol as a vehicle and a prodrug concentration of 5%, a flux of 3.6 μg/h/cm$^2$ was obtained. The good skin penetration of the octyloxycarbonyl prodrug derivative can most likely be attributed to its combination of high water and lipid solubility.

The feasibility of transdermal delivery for TRH via the prodrug approach of the present invention can be assessed by comparing the daily doses of TRH usually used via parenteral administration with those obtainable by transdermal delivery.

It the area of the patch for transdermal delivery is 20 cm$^2$ and if a flux of 16 μg/h/cm$^2$ is used it can readily be calculated that it is possible to deliver 320 μg TRH/h or 7.6 mg over 24 h. This amount is in the same range (0.5–5 mg) as that often given of TRH by infusion or injection during 24 h.

References Cited

Banks, W. A. & Kastin, A. J.: *Brain Res. Bull.* 15, 1985, 287–292.
Bassiri, R. M. & Utiger, R. D.: *J. Clin. Invest.* 52, 1973, 1616–1619.
Bauer, K.: *Biochimie* 70, 1988, 69–74.
Bauer, K., Nowak, P. & Kleinkauf, H.: *Eur. J. Biochem.* 118, 1981, 173–176.
Bundgaard, H. & Moss, J.: *J. Pharm. Sci.* 78, 1989, 122–126.
Duntas, L., Keck, F. S. & Pfeiffer, E. F.: *Dtsch. med. Wschr.* 113, 1988, 1354–1357.
Giralt, E., Ludevid, M. -D. & Pedroso, E.: *Bioorg. Chem.* 14, 1986, 405–416.
Griffiths, E. C.: *Nature* 322, 1986, 212–213.
Griffiths, E. C.: *Clin. Sci.* 73, 1987, 449–457.
Gronvald, F. C., Johansen, N. L. & Lundt, B. F.: In "Peptides, Structure and Biological Function. Proceed. Amer. Pept. Symp. 6th" (Eds.: Gross, E. & Meinhofer, F.), 1979, 309–312.
Gronvald, F. C., Lundt, B. F. & Johansen, N. L.: In "Peptides. Proceed. Eur. Pept, Symp. 16th, 1980" (Ed.: Brunfeldt, K.), Scriptor, Copenhagen, 1981, 706–710.
Hichens, M.: *Drug Metab. Rev.* 14, 1983, 77–98.
Iversen, E.: *J. Endocrin.* 118, 1988, 511–516.
Jackson, I. M. D.: *N. Engl. J. Med.* 306, 1982, 145–155.
Loosen. P. T.: *Prog. Neuro-Psychopharmacol. & Biol. Psychiat.* 12, 1988, S87–S117.
Matzner, M., Kurkjy, R. P. & Cotter, R. J.: *Chem. Rev.* 64, 1964, 645–687.
Metcalf, G.: *Brain Res. Rev.* 4, 1982, 389–408.
Morley, J. E., Garvin, T. J., Pekary, A. E., Utiger, R. D., Nair, M. G., Baugh, C. M. & Hershman, J. M.: *J. Clin. Endocrin. Metab.* 48, 1979, 377–380.
Wilk, S., Suen, C. -S. & Wilk, E. K.: *Neuropeptides* 12, 1988, 43–47.

We claim:

1. A derivative of TRH of the formula:

or wherein IA and IB are tautomers, or a mixture thereof, and $R_1$ is selected from the group consisting of methyl, ethyl, propyl, isopropyl, butyl, isobutyl, hexyl, octyl, cyclohexyl, benzyl, 2-chloroethyl, and 2-ethylhexyl; or a pharmaceutically acceptable acid addition salt thereof.

2. A pharmaceutical composition comprising a pharmaceutically acceptable carrier and a derivative according to claim 1.

3. The pharmaceutical composition as claimed in claim 2 in which the pharmaceutically acceptable carrier is a carrier for parenteral administration.

4. The pharmaceutical composition as claimed in claim 2 in which the pharmaceutically acceptable carrier is a carrier for nasal administration.

5. The pharmaceutical composition as claimed in claim 2 in which the pharmaceutically acceptable carrier is a carrier for buccal administration.

6. The pharmaceutical composition as claimed in claim 2 in which the pharmaceutically acceptable carrier is a patch for transdermal administration.

7. The pharmaceutical composition as claimed in claim 2 in which the pharmaceutically acceptable carrier is a carrier for oral administration.

* * * * *